United States Patent [19]

Eibofner et al.

[11] 4,260,381

[45] Apr. 7, 1981

[54] DENTAL HANDPIECE

[75] Inventors: Eugen Eibofner, Biberach; Ernst Strohmaier, Bad Schussenried, both of Fed. Rep. of Germany

[73] Assignee: Kaltenbach & Voight GmbH & Co., Biberach an der Riss, Fed. Rep. of Germany

[21] Appl. No.: 102,355

[22] Filed: Dec. 11, 1979

[30] Foreign Application Priority Data

Dec. 21, 1978 [DE] Fed. Rep. of Germany ....... 2855359

[51] Int. Cl.³ .............................................. A61C 3/06
[52] U.S. Cl. ................................... 433/126; 433/133
[58] Field of Search ............................... 433/126, 105

[56] References Cited

U.S. PATENT DOCUMENTS

| | | | |
|---|---|---|---|
| 3,835,858 | 9/1974 | Hagen | 433/126 |
| 4,021,917 | 5/1977 | Nakanishi | 433/126 |

*Primary Examiner*—Robert Peshock
*Attorney, Agent, or Firm*—Scully, Scott, Murphy & Presser

[57] ABSTRACT

A dental handpiece consisting of a driving sleeve which includes a driving arrangement, a base sleeve and a head sleeve including a dental work tool. At least the base sleeve and the head sleeve are detachably interconnected for the purpose of exchanging the head sleeve, and in which a shaft is supported within the base sleeve which is in rotational connection with the driving arrangement in the driving sleeve, and which is provided with a rotation-transmitting element for engagement with a shaft component supported within the head sleeve.

17 Claims, 13 Drawing Figures

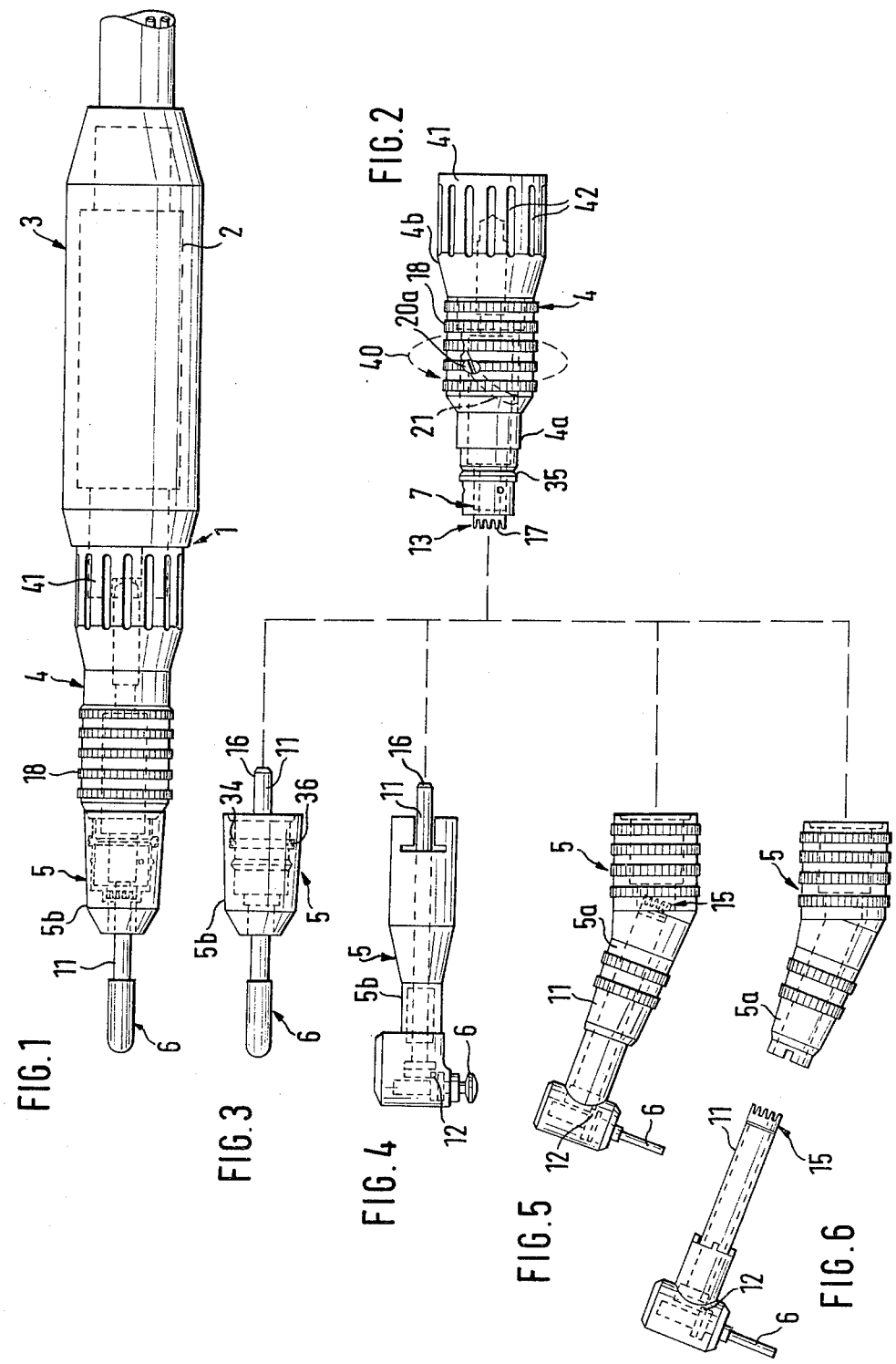

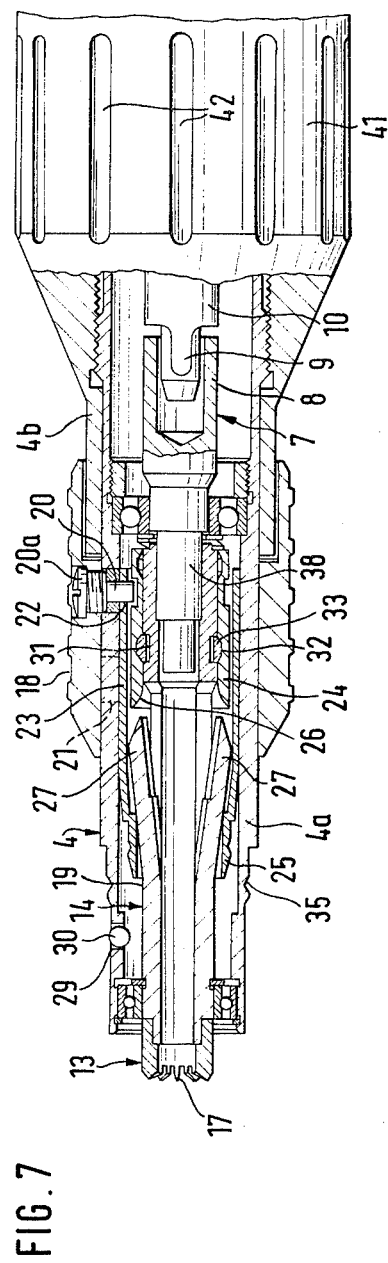
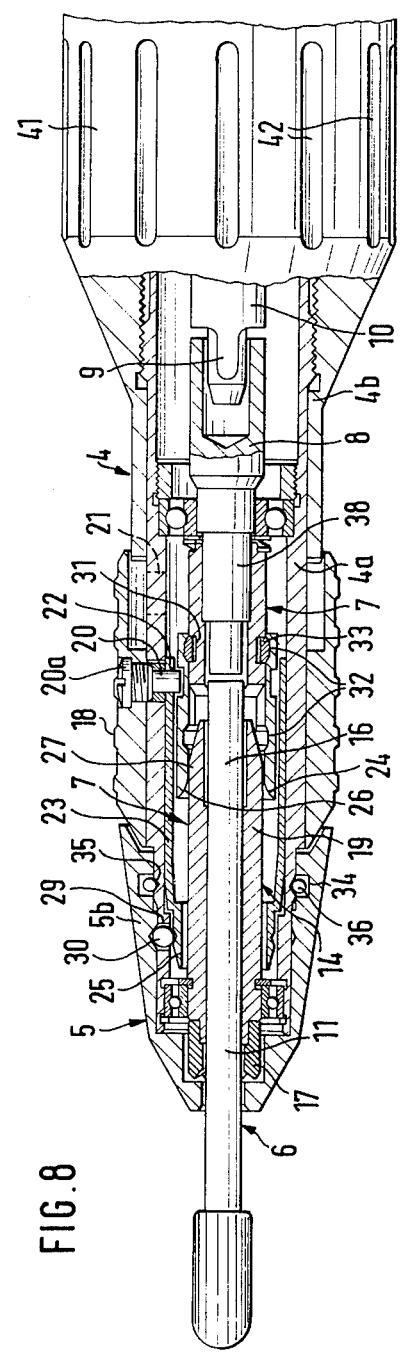
FIG.7
FIG.8

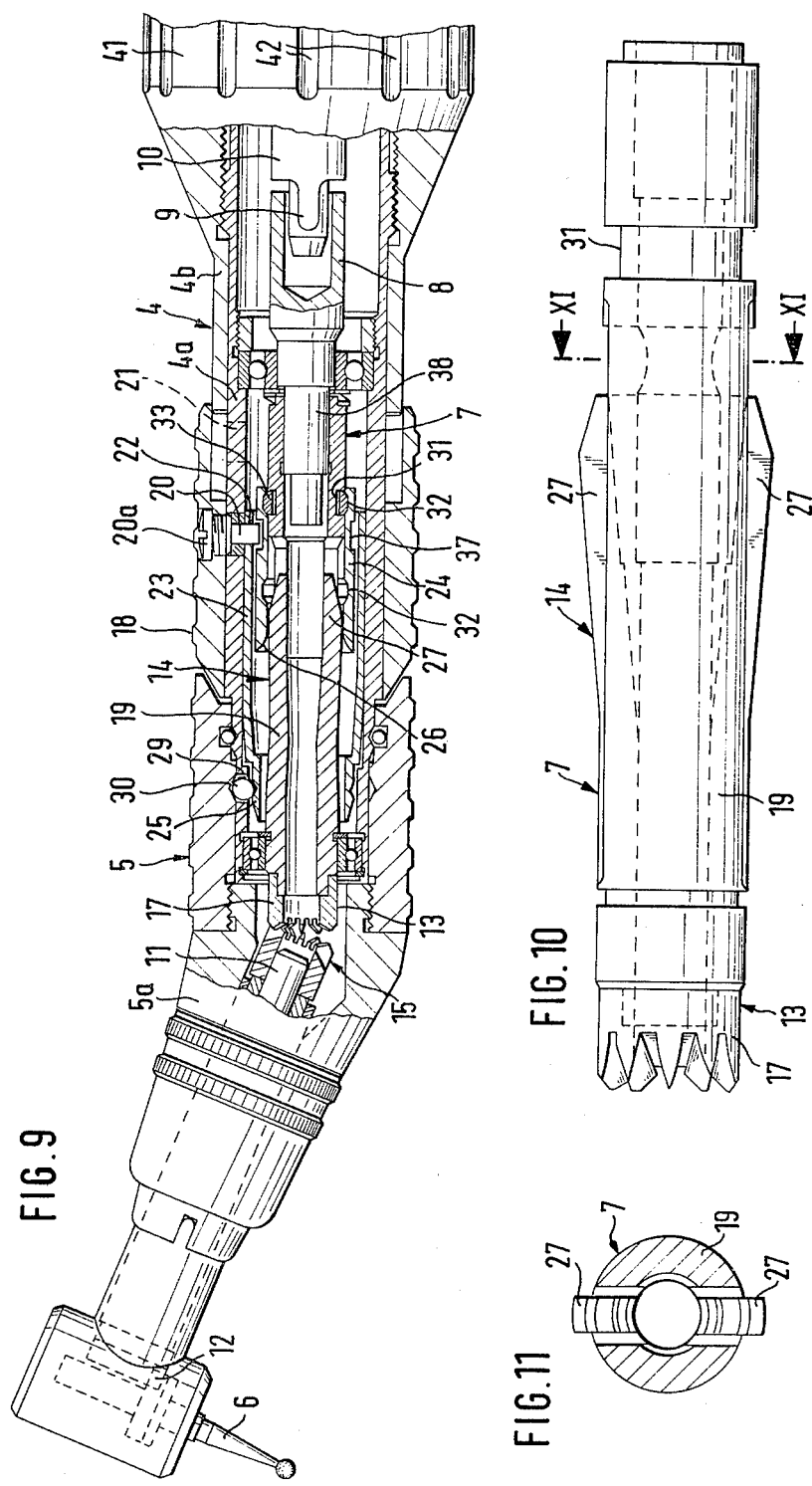

FIG. 12
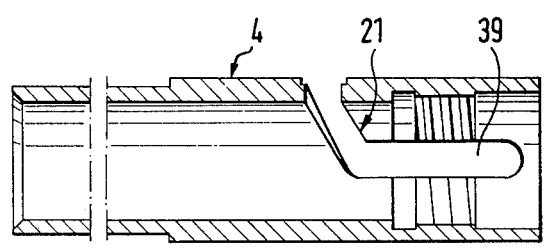
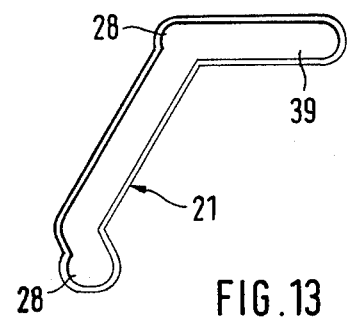
FIG. 13

DENTAL HANDPIECE

BACKGROUND OF THE INVENTION

1. Field of the Invention

The present invention relates to a dental handpiece consisting of a driving sleeve which includes a driving arrangement, a base sleeve and a head sleeve including a dental work tool, wherein at least the base sleeve and the head sleeve are detachably interconnected for the purpose of exchanging the last-mentioned, and in which a shaft is supported within the base sleeve which is in rotational connection with the driving arrangement in the driving sleeve, and which is provided with a rotation-transmitting element for engagement with a shaft component supported within the head sleeve.

2. Discussion of the Prior Art

A handpiece of that type has become known from German Laid-open Patent Application No. 16 25 749. In this known handpiece the rotation-transmitting element of the shaft which is supported within the base sleeve consists merely of an engaging element which is constructed as a drive gear and is arranged at the drive-sided shaft end so that only such head sleeves can be connected to the base sleeve which are equipped with a complimentary engaging element at the drive-sided end of the shaft portion supported interiorly thereof which is adapted to be brought into engagement with the above-mentioned engaging element. Head sleeves whose shaft portion at the drive-sided end thereof do not evidence a complementary engaging element and which have a blunt end, can as a result not be connected with the base sleeve of the known handpiece.

SUMMARY OF THE INVENTION

Accordingly, it is an object of the present invention to provide a dental handpiece of the above-mentioned type which, irrespective as to whether the drive-sided end of the shaft portion which is arranged in the exchangeable head sleeve incorporates a complementary engaging element, or whether the axially non-displaceable shaft component of the respective head portion ends blunt at the drive-sided end thereof, can always be connected to a head sleeve type which is desired by the dentist.

The advantages which are achieved by the invention can be essentially ascertained in that, upon connection of a head-sleeve of the first type which includes a shaft portion having a complementary engaging element, there automatically as in the above-mentioned known handpiece, the engaging element on the shaft of the base sleeve will come into engagement with the complementary engaging member on the shaft component of the head sleeve and wherein, without further measures, in lieu of a head sleeve of this first type there can be attached another head sleeve, in essence a head sleeve of the second type, effectively with a drive-sided blunt ending shaft portion, to the same base sleeve, possibly while still connected with the same driving sleeve. For this purpose there need merely be actuated from the externally accessible outer shifting element whereby the gripping arrangement opens for the receipt of the blunt-shaped end of the shaft portion and, respectively, the opened gripping arrangement will close for the gripping of the mentioned end portion of the shaft. This will extensively widen the range of application of the unit which is constituted of the base sleeve and the driving sleeve. In addition thereto, it is also possible that the base sleeve, notwithstanding its mentioned dual function, can in an advantageous manner be constructed as a smaller compact component. For the receipt of the above-mentioned shaft portion end within the gripping arrangement, which is more advantageous, either the shaft portion end can project out of the drive-sided end of the head sleeve or the gripping arrangement from the power take-off end of the head sleeve by a length which will provide for an effective gripping engagement.

The gripping arrangement can consist of a collet. When constructed as a friction collet, the shifting element includes an axially extending push rod for ejecting the work tool gripped in the collet under the effect of adhesive friction of the inner wall thereof which is, for example, formed of rubber, plastic material or another resilient material constituted in a wall of the collet in the last clamped in tool. However, also suitable is a construction as a clamping collet which includes clamping tongues wherein the shifting element operates in the context of assuming the clamping action on the clamping tongues.

The engaging element and complementary engaging element may suitably be constructed, for example, as spherical planetary gear drive components or, even more suitably, as spur gears.

BRIEF DESCRIPTION OF THE DRAWINGS

Reference may now be had to preferred exemplary embodiments of the invention, taken in conjunction with the accompanying drawings; in which:

FIG. 1 illustrates a longitudinal side view of a dental handpiece;

FIG. 2 illustrates the base sleeve of the handpiece of FIG. 1 in a longitudinal side view;

FIGS. 3 and 4, respectively, show different embodiments of a first type of head sleeve in side views;

FIG. 5 is a side view of an embodiment of a second type of head sleeve;

FIG. 6 shows the head sleeve of FIG. 5 in a disassembled condition;

FIG. 7 is a part-sectional view of the base sleeve;

FIG. 8 illustrates the base sleeve of FIG. 7 with head sleeve of the first type pursuant to FIG. 3 connected thereto;

FIG. 9 illustrates the base sleeve of FIG. 7 with a head sleeve of the second type pursuant to FIGS. 5 and 6 shown connected thereto;

FIG. 10 illustrates, on an enlarged scale, a tubular clamping collet which is insertable into the base sleeve;

FIG. 11 is a section taken along line XI—XI in FIG. 10;

FIG. 12 is a sectional view of only the base sleeve; and

FIG. 13 is a development of the slot which is provided in the base sleeve.

DETAILED DESCRIPTION

The dental handpiece 1 consists of three mutually interconnected cylindrical sleeves or casings, in essence, a driving sleeve 3 which includes a power or driving arrangement 2, a base sleeve 4 which forms a coupling member, a head sleeve 5 which includes a rotatable dental tool 6, for instance, a drill, a polishing tool or the like. The driving arrangement 2 can be an air motor, an electrical miniature motor, the connecting element of a flexible shaft, or a drive cord or the like. The base sleeve 4, the head sleeve 5 and the driving sleeve 3 are interconnected so as to extend coaxially with respect to each other. At least the connection between the base sleeve 4 and the head sleeve 5, possibly while facilitating mutual rotational displacement between the two sleeves, is constructed so as to be detachable for the purpose of exchanging the head sleeve. Supported within the base sleeve 4 is a shaft 7 which is in rotational connection with the driving arrangement 2 of the driving sleeve 3. The shaft 7 can be integral with the driving arrangement 2. However, pursuant to FIGS. 7, 8 and 9, the shaft 7 possesses an engaging element 8 at its drive-sided end which stands in engagement with a complementary engaging element 9 on the drive shaft 10 of the driving arrangement 2. The shaft 7 is provided with a rotation-transmitting element for engagement with shaft portion 11 which is supported within the head sleeve 5, which shaft portion in accordance with FIGS. 4, 5, 6 and 9 drives the shaft of the work tool 6 through a drive 12, or pursuant to FIGS. 1, 3 and 8 forms the shaft of the work tool 6.

Two types 5a and 5b of head sleeves can be connected with the base sleeve. In the first head sleeve type 5a, the shaft portion 11 pursuant to FIGS. 5, 6 and 9 which supported interiorly of the head sleeve possess a complementary engaging element 15 at the drive-sided end thereof, whereas in the second head sleeve type 5b, the shaft portion 11 pursuant to FIGS. 1, 3, 4 and 8 which is supported interiorly of the head sleeve possesses a blunt-shaped drive-sided end 16, in effect, one which is not provided with a complementary engaging element.

The rotation-transmitting element of the shaft 7 of the base sleeve 4 consists of two rotation-transmitting components 13 and 14 of which one is presently utilized in the arrangement of one of the two head sleeve types 5a or 5b. For the first head sleeve type 5a, the one rotation-transmitting component 13 consists of an engaging element 17 arranged on the power takeoff-sided end of the shaft 7 of the base sleeve 4 for engagement into the above-mentioned complementary engaging element 15; whereas for the second head sleeve type 5b, the other rotation-transmitting component 14 is formed by gripping arrangement 19 adapted to be actuated by an externally operable shifting element 18 for the gripping of the blunt-shaped shaft portion end 16, and which is open for the insertion of the blunt-shaped shaft portion end 16. The complementary engaging element 15 and engaging element 17 are presently formed by a spur gear on the shaft portion 11 or on the shaft 7. The head sleeve 5 which is illustrated in FIG. 5 can be disassembled as shown in FIG. 6, for example, in order to be able to exchange the shaft portion 11 with another shaft portion having a complementary engaging element 15 leading to a "stepped-up" or "stepped-down" gearing.

The shifting element 18 which is arranged exteriorly of the base sleeve 4 is axially movable relative to the base sleeve 4 and possesses a radial pin 20 directed towards the interior of the base sleeve 4, which engages through the slot 21 in the base sleeve allowing for the mentioned axial movement, and furthermore through an aperture 22 of a first latching element 23 arranged within the base sleeve into a second latching element 24 which is also arranged within the base sleeve, while taking along the two latching elements 23, 24 during the mentioned actual movement. The two latching elements 23, 24 can be constituted of a common unitary member or, as illustrated, of two separate components. The radial pin 20 consists of a screw which extends through the shifting element 18 and which can be threaded together therewith, and whose head is designated with reference numeral 20a. The first latching element 23 possesses an actuating component 25 for the latched connection of the head sleeve 5 to the base sleeve 4, whereas the second latching element 24 is provided with an actuating member 26 for effecting of the gripping position of the axially immovable gripping arrangement 19. This embodiment has the attendant advantage that only a single handle or grip, in effect, that of the shifting element 18, is provided for carrying out two functions, namely, one for the head sleeve latching or otherwise, selectively in accordance with the head sleeve type 5a or 5b employed, for gripping of the work tool. With a suitable construction of the head sleeve, both functions can also be concurrently effectuated through manipulation of the shifting element 18.

The gripping arrangement 19 is formed by a clamping collet partially forming the shaft 7 and evidencing clamping jaws or tongues 27.

The shifting element 18 consists of a rotatable ring encompassing the base sleeve 4, whereby the slot 21 which traversed by the radial pin 20 of the base sleeve 4 and allowing for the axial movement of the rotatable ring is in a form of a screw thread. The screw thread-like shaped slot 21 possesses at each of its ends a latching section 28 without an increase in the circumferential direction (FIG. 13) for the latching of the radial pin 20 in the two rotational end position of the rotatable ring forming the shifting element 18.

The first latching element 23, which is axially displaceable through rotation of the rotatable ring by means of the radial pin 20, consists of a thrust sleeve which, together with the rotatable ring forming the shifting element 18, is arranged so as to be rotatable and which at its power takeoff end evidences an outer annular tapered surface expanding from the sleeve end and forming the actuating member 25 for the latching of the head sleeve, which is adapted to be brought into engagement during the rotation of the rotatable ring with latching members 30 arranged in the apertures 29 of the base sleeve 4 and preferably formed as balls, and to press these outwardly against the inner wall of the head sleeve 5 into a clamping latching position.

The second rotatable ring which through rotation forms the shifting element 18 by means of the radial pin 20 axially displacing the latching element 24 consists of a thrust sleeve which encompasses the tubular collet, and which at least in the gripped position of the gripping arrangement 19 is arranged so as to be commonly rotatable with the latter and evidences at the power takeoff end an inner annular wedge or taper surface expanding from the sleeve end constituting the actuating member 26 for effecting the gripping position of the gripping arrangement 19, which during the rotation of the rotatable ring with the projection forming, outwardly resiliently prestressed clamping jaws 27 press these inwardly against the shaft portion 11 of the head sleeve 5 in the area of the gripping arrangement 19 into the gripping position. The two thrust sleeves which form the latching elements 23 and 24 are arranged coaxially whereby the thrust sleeve forming the first latching element 23 encompasses the thrust sleeve forming the second latching element 24.

In order to prevent binding of the radial pin 20 in the rotational end positions of the rotatable ring which forms the shifting element 18, it is suitable that the shaft 7, or the collet forming the gripping arrangement 19 evidences an external annular groove 31 in the second latching element 24 formed by the thrust sleeve in the axial region extending over the shifting element 18 in all rotational positions, and in which a spring ring 33 is arranged so as to come into engagement in one of the two rotational end positions of the rotatable ring in corresponding annular groove 32 in the mentioned thrust sleeve. In the above-mentioned two rotated end positions, the spring ring 33 which always constantly remains within the annular groove 31 will engage into the left or right annular 32 as shown in the drawing.

For the additional latching of the head sleeve 5, in effect the securing with respect to the base sleeve 4 prior to carrying out the latching through actuation of the shifting element 18, it is suitable when, in accordance with FIGS. 3, 7 and 8, there is provided in the head sleeve 5 an inner completely or partially extending annular groove 34 in which, upon the plugging together of the head sleeve and the base sleeve there is arranged a spring element 36 coming into engagement with a corresponding external groove 35 in the base sleeve 4. It is suitable that the inner annular groove 34 in the head sleeve 5 extends along the full circumference and the resilient element 36 is constructed as a spring ring.

As illustrated in FIGS. 7 to 9, the thrust sleeve forming the second latch element 24 is provided with an external annular groove 37 for engagement with the radial pin 20 of the shifting element 18.

Inserted or threaded into the drive-sided end of the tubular collet which forms the gripping arrangement 19 is a shaft section 38 in rotational connection with the driving arrangement 2 of the driving sleeve 3 through the engaging elements 8, 9, together with the collet, and forming the shaft 7 supported within the base sleeve 4.

In order to facilitate a simply effected exchange of the collet forming the gripping arrangement 19, there is provided an arrangement wherein, in accordance with FIGS. 12 and 13, the slot 21 in the base sleeve 4 constructed in a type of screwline has at its drive-sided end a linear extension 39 of such a length extending axially towards the drive-sided end of the base sleeve, so that after movement of the radial pin 20 into the latching section 28 shown towards the right in FIGS. 12 and 13, there is still a movement of the rotatable ring in an axial direction towards the drive-sided end of the extension 39 and thereafter, or concurrently, there becomes possible a radial deflection of the shaft 7 of the base sleeve 4 with the release from engagement of the radial pin 20 in the second latching element 24 and, through pull, an axial movement of the shaft 7 in a direction toward the drive-sided end out of the base sleeve 4 which has been detached from the driving sleeve 3. Arranged hereby is the one drive-sided latching section 28 at the transition of the screwline-shaped slot 21 into the linear extension 39, and the other power takeoff-sided latching section 28 at the power takeoff-sided end of the screwline-shaped slot 21.

The base sleeve 4 consists, for instance, of two mutually interconnected, screwed together individual sleeves, namely, of the guide sleeve 4a evidencing the slot 21, the external groove 35, and the apertures 29; and the retaining sleeve 4b which is to be held fast upon rotation of the shifting element 18 formed by the rotatable ring when rotated in the direction of the arrow 40 in FIG. 2. For the provision of an improved retention, the retaining sleeve 4b possesses an enlarged diameter portion 41 which has a ribbed surface 42. Prior to the mentioned axial outward movement of the shaft 7, for example, through exerting a pull on the shaft section 38, the retaining sleeve 4b is suitably separated and removed from the guide sleeve 4a.

What is claimed is:

1. In a dental handpiece including a driving sleeve having driving means; a base sleeve; a head sleeve having a dental work tool attachable thereto, at least said base sleeve and head sleeve being detachably interconnected to facilitate exchange of said head sleeve; a shaft supported in said base sleeve and rotatably connected with said driving means; and rotation-transmitting means on said shaft engageable with a shaft member supported in said head sleeve; the improvement comprising: said rotation-transmitting means consisting of first and second rotation-transmitting components of which one is presently utilized in the application of one of two differently constructed types of head sleeves, said first rotation-transmitting component, at a shaft component arranged interiorly of the first type of head sleeve and having a complementary engaging means at the drive-sided end, being constituted of an engaging means on the power takeoff end of the shaft in said base sleeve and adapted for engagement in said engaging means; and said second rotation-transmitting component, at a shaft component having a blunt-shaped drive-sided end arranged interiorly of the second type of head sleeve, being constituted of a gripping arrangement open towards the power takeoff end and actuatable by an external shifting element for gripping the blunt-shaped shaft component end.

2. Dental handpiece as claimed in claim 1, said engaging means and said complementary engaging means each comprising a spur gear.

3. Dental handpiece as claimed in claim 1 or 2, said shifting element being axially movable relative to said base sleeve, a slot in said base sleeve; a radial pin in said base sleeve extending through said slot allowing said axial movement; a first latching means in said base sleeve having an aperture therethrough; and a second latching means, said radial pin traversing said aperture and engaging said second latching means while taking along said first and second latching means during said axial movement, said first latching means including an actuating component for the latched fastening of said head sleeve on said base sleeve, and said second latching means including an actuating component for effecting the gripping position of the axially immobile arranged gripping arrangement.

4. Dental handpiece as claimed in claim 1, said gripping arrangement comprising a collet at least partially forming the shaft of said base sleeve.

5. Dental handpiece as claimed claim 4, said collet comprising a clamping collet.

6. Dental handpiece as claimed in claim 3, said shifting element comprising a rotatable ring encompassing said base sleeve, said slot in said base sleeve having a screwline-shaped configuration.

7. Dental handpiece as claimed in claim 6, said slot having latching sections at both ends thereof without increasing in a circumferential direction for the latching of said radial pin in both rotational end positions of said rotatable ring.

8. Dental handpiece as claimed in claim 3, said first latching means comprising a thrust sleeve arranged for rotation with said rotatable ring, said latching means including an external annular tapered surface at the power-takeoff end thereof and expanding from the sleeve end so as to form said actuating component for latching of said head sleeve; latching members arranged in recesses within said base sleeve being engageable by said actuating means during rotation of said rotatable ring so as to be pressed against the inner wall of said head sleeve into a latching position.

9. Dental handpiece as claimed in claim 3, said second latching means comprising a thrust sleeve having an inner annular tapered surface at the power-takeoff end thereof expanding from the sleeve end so as to form the actuating component for effecting the gripping position of said gripping arrangement; said rotatable ring including outwardly projecting, resiliently prestressed clamping tongues adapted to be engaged by said actuating component so as to be inwardly pressed into a gripping position against the shaft portion of said head sleeve in the region of said gripping arrangement.

10. Dental handpiece as claimed in claim 8 or 9, wherein said thrust sleeve are arranged coaxially within each other.

11. Dental handpiece as claimed in claim 9, said shaft having an external annular groove in the axial region in which the thrust sleeve forming the second latching means is superimposed in all rotational positions of the rotatable ring forming said shifting element; and a spring ring; said spring ring being in inner annular grooves in said thrust sleeve, said spring ring coming into engagement with said external groove in one of the two rotational end positions of said thrust sleeve.

12. Dental handpiece as claimed in claim 1, comprising an at least partially extending annular inner groove in said head sleeve; and spring means in said groove adapted to engage a corresponding external groove in said base sleeve.

13. Dental handpiece as claimed in claim 12, wherein said inner annular groove entirely encompasses the periphery of said head sleeve, and said spring means comprises a spring ring.

14. Dental handpiece as claimed in claim 9, said thrust sleeve forming said second latching means including an encompassing outer annular groove for engaging said radial pin.

15. Dental handpiece as claimed in claim 4, said collet being tubular; and a shaft section, forming together with said collet the shaft supported within said base sleeve, being fixed inserted in the drive-sided end of said tubular collet and being in rotational connection with the driving means in said driving sleeve.

16. Dental handpiece as claimed in claim 3, said screwline-shaped slot in said base sleeve including a linear extension axially extending towards the drive-sided end of said base sleeve of a length facilitating, at an axial movement of the rotatable ring towards the drive-sided end of the extension, a radial deflection of the shaft of said base sleeve with release of the engagement of said radial pin in said second latching means and an axial outward movement of said shaft in a direction towards the drive-sided end out of the base sleeve released from said driving sleeve.

17. Dental handpiece as claimed in claim 7, wherein one said latching section is arranged at the transition of said screwline-shaped slot into said linear extension and the other latching section is arranged at the power-takeoff end of the screwline-shaped slot.

* * * * *